(12) United States Patent
Tarjan et al.

(10) Patent No.: US 7,043,292 B2
(45) Date of Patent: May 9, 2006

(54) SINGLE OR MULTI-MODE CARDIAC ACTIVITY DATA COLLECTION, PROCESSING AND DISPLAY OBTAINED IN A NON-INVASIVE MANNER

(76) Inventors: Peter P. Tarjan, 8526 SW. 94th St., Miami, FL (US) 33156; Chih-Cheng Lu, 214 Lie-Nan Street, Kaohsiung (TW) 803; Walter Besio, 775 Meadowlark Dr., Lakeland, FL (US) 33809-4625

( * ) Notice: Subject to any disclaimer, the term of this patent is extended or adjusted under 35 U.S.C. 154(b) by 677 days.

(21) Appl. No.: 10/176,944

(22) Filed: Jun. 21, 2002

(65) Prior Publication Data
US 2003/0236466 A1    Dec. 25, 2003

(51) Int. Cl.
*A61B 5/402*    (2006.01)
(52) U.S. Cl. ................ 600/509; 600/512; 600/528
(58) Field of Classification Search ............. 600/508, 600/509, 512, 528
See application file for complete search history.

(56) References Cited

U.S. PATENT DOCUMENTS

| | | | |
|---|---|---|---|
| 6,014,582 A * | 1/2000 | He | 600/544 |
| 6,780,152 B1 * | 8/2004 | Ustuner et al. | 600/443 |
| 2002/0128565 A1 * | 9/2002 | Rudy | 600/509 |

OTHER PUBLICATIONS

W.G. Besio, C.C. Lu and P. P. Tarjan, "A Feasibility Study for Body Surface Cardiac Propagation Maps of Humans from Lapacian Moments of Activation", *Electromagnetics*, 21:621-632, 2001.

(Continued)

*Primary Examiner*—Jeffrey R. Jastrzab
(74) *Attorney, Agent, or Firm*—Thomas R. Vigil; Welsh & Katz, Ltd.

(57) ABSTRACT

The method of presenting concurrent information about the electrical and mechanical activity of the heart using non-invasively obtained electrical and mechanical cardiac activity data from the chest or thorax of a patient comprises the steps of: placing at least three active Laplacian ECG sensors at locations on the chest or thorax of the patient; where each sensor has at least one outer ring element and an inner solid circle element, placing at least one ultrasonic sensor on the thorax where there is no underlying bone structure, only tissue, and utilizing available ultrasound technology to produce two or three-dimensional displays of the moving surface of the heart and making direct measurements of the exact sites of the sensors on the chest surface to determine the position and distance from the center of each sensor to the heart along a line orthogonal to the plane of the sensor and create a virtual heart surface; updating the measurements at a rate to show the movement of the heart's surface; monitoring at each ultrasonic sensor site and each Laplacian ECG sensor site the position and movement of the heart and the passage of depolarization wave-fronts in the vicinity; treating those depolarization wave-fronts as moving dipoles at those sites to create images of their movement on the image of the beating heart's surface; and, displaying the heart's electrical activity on the dynamically changing image of the heart's surface with the goal to display an approximation of the activation sequence on the beating virtual surface of the heart

16 Claims, 2 Drawing Sheets

OTHER PUBLICATIONS

Chih-Cheng Lu and Peter P. Tarjan, PhD, "An Ultra-High Common-Mode Rejection Ratio (CMRR) AC Instrumention Amplifier for Laplacian Electrocardiographic Measurement", *Jan./Feb. Issue of Instrumentation Research*, pp. 76-83.

G.E. Antonioli, P.P. Tarjan, C.C. Lu, T. Toselli and M.S. Argnani, "Non-Invasive Detection of Moment of Activation Using Laplacian Cardiac Electrogram Body Surface Mapping System", *Jun. 1999 article from Progress in Biomedical Research*, pp. 382-387.

M.S. Argnani, MD, G.E. Antonioli, MD, C.C. Lu and P.P. Tarjan, PhD, "First Clinical Series with Laplacian Electrograms with Active Concentric Ring Sensors", *HeartWeb vol.4 No. 3 Jan. 1999*, pp. 1-6.

C.C. Lu, R. Plourde, W.Y. Fang, S. Uhlhorn, P.P. Tarjan, "Laplacian Electrocardiograms with Active Electrodes", *IEEE Publication*, 4 pages total.

* cited by examiner

FIG. 1c (shows the movement and changing shape of the virtual heart along with the isochronal lines. The dashed arrow indicates the progression of time and the solid arrows show the direction of the movement of the heart.)

Fig. 2a	Fig. 2b $V_{sensed} = 0.5(V_1 + V_3) - V_2$ $\quad = 0.5\,[(V_1 - V_2) - (V_2 - V_3)]$ $\quad \approx 0.5\,[\,\Delta V_{1,2}\big|_{(r_1+r_2)/2} - \Delta V_{2,3}\big|_{(r_2+r_3)/2}\,](\Delta r)$

$\quad \approx 0.5\,[\,\Delta^2 V_{1,3\text{-}2}\,](\Delta r)^2 \approx 0.5(\Delta r)^2 \nabla^2 V$ $V_{sensed} = 0.5(V_1 - V_3)$ $\quad = 0.5\nabla(V_{1,3})(2\Delta r)$ $\quad \approx \nabla V(\Delta r)$

Fig. 3

SINGLE OR MULTI-MODE CARDIAC ACTIVITY DATA COLLECTION, PROCESSING AND DISPLAY OBTAINED IN A NON-INVASIVE MANNER

BACKGROUND OF THE INVENTION

1. Field of the Invention

The present invention relates to the concurrent detection of the electrical and mechanical activity of the heart by non-invasive means, the processing of the data and its presentation to physicians and other health care providers with the objectives to diagnose a condition, monitor a condition, guide a therapeutic intervention, or provide prognosis regarding some pathology.

2. Description of the Prior Art

The heart is a complex pump that engineers may view as an electromechanical device. Its pumping performance varies from moment to moment or beat to beat as it reflects the dynamic and emotional state of the organism, a human or an animal, that it serves. The natural control of the heart is partly traced to the electrical activity of its tissues, which are partly influenced by the central nervous system, partly by chemical influences delivered through the blood, partly by the state of its own coronary circulation, as well as its past history, such as myocardial infarcts, occlusion of coronary arteries, trauma, and so on. The diagnosis and treatment of pathological heart function are dependent on measurements of these influences and on the hemodynamic performance of the pump.

The present invention in its preferred form relates to the concurrent detection of the electrical and mechanical activity of the heart by non-invasive means, the processing of the data and its presentation to physicians and other health care providers with the objectives to diagnose a condition, monitor a condition, guide a therapeutic intervention, or provide prognosis regarding some pathology. It could also be utilized to query information from other electrically active organs. This method is suitable for non-biological applications where electromagnetic radiation and physical position are to be sensed remotely from a source or multiple sources. This, for example could be accomplished with a plurality of the Laplacian sensors and the sonar of a submarine.

The performance of the human heart in health and disease has been quantitatively studied at least since William Harvey presented "De Motu Cordis" early in the $17^{th}$ century. Non-invasive means for gathering such data regarding heart parameters have been used for more than a century. These means include auscultation, listening to the sounds from the chest with a stethoscope, recording roentgenograms and cine-radiograms (early $20^{th}$ c.), electrocardiograms or ECGs (early $20^{th}$ c.), pressure recordings, impedance cardiograms (Kubicek et al., mid-$20^{th}$ c.), electro-kymograms (cca. 1950), ballistocardiograms (cca. 1950), among others. Simultaneous access to localized electrical and mechanical activity has been elusive. ECGs provide considerable detail about the electrical activity of heart tissues, but very little about the heart's pumping. Body surface electrograms (BSE) and vectorcardiograms (VCG) showed great promise, but for various reasons have not become standard tools in cardiology. Ultrasonic techniques have emerged over the past two decades providing fine details about the architecture and dynamics of the heart, non-invasively. Various algorithms have evolved to quantify these aspects. Despite these advances, the simultaneous display and quantitative presentation of the electrical and mechanical activities have been inadequate, limited to a surface ECG recorded along with sophisticated ultrasonic studies, or, alternately, blood pressure monitoring during a sophisticated electrophysiologic study.

ECGs and BSEs are recorded according to certain conventions. A minimal ECG system comprises three electrodes on the body surface, two of which, the "active" electrodes, are connected to a differential amplifier and the third one serves as a potential reference, usually connected to ground. Ideally, the potential difference between the two active electrodes is amplified. The record is called bipolar when the active electrodes are far apart on the chest, for instance, placed on the left and right shoulders. The record is unipolar when there is one "active" electrode that is placed at one of many specific anatomic landmarks, the V-lead positions, near the heart, while the second electrode is not really active as it is the average of the potentials at three sites, the left and right arms and the left leg; this reference is called the Wilson terminal. This mode of recording is rather sensitive to the placement of the active electrode and allows identification of parts of the heart where the electrical activity is abnormal.

In BSE the number of active electrodes is large, usually ranging from 30 upward to more than 100; each one provides information about activity in its own vicinity. However, the signal is only moderately responsive to nearby electrical activity and it is often hard to distinguish local from more distant activity as the amplitude of the detected signal is proportional to the volume of contributing tissue mass and inversely proportional to its distance to the electrode.

Bipolar recordings with closely spaced electrodes are more sensitive to local activities but they are also selective with respect to the direction of travel of the electrical activity in the tissues. The electrical source of the signal travels inside the body and within the heart, and may be represented by an equivalent mobile dipole. When the line connecting the surface electrodes coincides with the travelling direction of the source, then the signal is strongest, when those are perpendicular, the signal vanishes. For this and other reasons, concentric electrodes have been used at least since 1950, when Fattorusso et al. reported that supplementary information may be extracted with such electrodes.

BRIEF HISTORY OF RELATED TECHNOLOGIES

Around 1984, the present inventor, Peter Tarjan proposed the use of three concentric ring electrodes in a bipolar connection (+−+) to record the local electrical signals generated by the heart. ("Local," implies the vicinity of the sensor.). Prior to 1987, those chronically implanted epicardial sensors were tested successfully in dogs to detect, acutely and chronically, artificially induced arrhythmias, for up to three month. The results were first presented in Boston (NASPE, 1987) and in Jerusalem (World Congress in Cardiac Pacing, 1987).

M. Kaufer and L. Rasquinha worked on the continuation of the project at the University of Miami with Peter Tarjan. Both their M.S. theses dealt with tripolar concentric sensors, with emphasis on the sensor being in contact with the epicardium. Subsequently, the passive 3-ring sensors were tested for surface recordings from the torso, without success. Those sensors were also evaluated on the human forehead for the purpose of sensing volitional facial maneuvers. This work led to a U.S. Pat. No. 5,817,030 assigned to the University of Miami, in October 1998.

A compact "active" sensor with its own batteries was developed next for surface recordings of the heart's activity using similar 3-ring sensors. Two or three concentric electrodes provide signals in proportion to the first and second spatial derivatives of the surface potential on the torso. The three electrode configuration uses the inner and outer electrodes shorted to each other to enhance spatial selectivity.

A doctoral dissertation by a Mr. Chih-Cheng Lu advanced the development of the three-ring sensors. The prototypes of the sensors and the signal processing software were tested on healthy volunteers and more than 60 patients. The objective was to record the second spatial derivative of the surface potential directly from the chest. Others, especially B. He, have also obtained such surface plots by computing these derivatives from digitized surface potential maps.

Set forth below is a bibliography of the prior art literature references related to heart activity monitoring and computed Laplacian electrograms.

Fattorusso, V., M. Thaon, and J. Tilmant, *Contribution a l'etude de l'electrocardiogramme precordial*. Acta Cardiol, 1949. 4: p. 464–487.

Fattorusso, V. and J. Tilmant, *Exploration du champ electrique precordial a l'aide de deux electrodes circulaires, concentriques et rapprochees*. Arch. Mal de Coeur, 1949. 42: p. 452–455.

He, B., et al., *A comparison of volume conductor effects on body surface Laplacian and potential ECGs: a model study*. Computers in Biology and Medicine, 1997. 27(2): p. 117–127.

He, B., Y. B. Chernyak, and R. J. Cohen, *An equivalent body surface charge model representing three-dimensional bioelectrical activity*. IEEE Transactions on Biomedical Engineering, 1995. 42(July): p. 637–646.

He, B. and R. J. Cohen, *Body surface Laplacian mapping in man*. Annual International Conference of the IEEE Engineering in Medicine and Biology Society, 1991. 13: p. 784–786.

He, B. and R. J. Cohen, *Body surface Laplacian ECG mapping*. IEEE Transactions on Biomedical Engineering, 1992. 39(2): p. 1179–1191.

He, B. and R. J. Cohen, *Body surface Laplacian mapping of cardiac electrical activity*. The American Journal of Cardiology, 1992. 70(December): p. 1617–1620.

He, B. and R. J. Cohen, *Body surface Laplacian electrocardiographic mapping-a review*. Critical Reviews in Biomedical Engineering, 1995. 23(5&6): p. 475–510.

He, B., et al., *Body surface Laplacian mapping of cardiac excitation in intact pigs*. PACE, 1993. 16(May): p. 1017–1026.

He, B. and D. Wu, *A bioelectric inverse imaging technique based on surface Laplacian*. IEEE Transactions on Biomedical Engineering, 1997. 44(7): p. 529–538.

Johnston, P. R., *The potential for Laplacian maps to solve the inverse problem of electrocardiography*. IEEE Transactions on Biomedical Engineering, 1996. 43(4): p. 384–393.

Johnston, P. R., *The Laplacian inverse problem of electrocardiography: An eccentric spheres study*. IEEE Transactions on Biomedical Engineering, 1997. 44(7): p. 539–548.

Oostendorp, T. F. and A. v. Oosterom, *The surface Laplacian of the potential: theory and design*. IEEE Transactions on Biomedical Engineering, 1996. 43(4): p. 394–405.

Oosterom, A. v. and J. Strackee, *Computing the lead field of electrodes with axial symmetry*. Medical & Biological Engineering & Computing, 1983. 21(July): p. 473–481.

Bonilla, S. J., L. Rasquinha, and P. P. Tarjan. *Tripolar concentric ring electrodes for detecting forehead myoelectric potentials*. in *Annual International Conference of the IEEE Engineering in Medicine and Biology Society*. 1995. Montreal, Que, Canada.

Kaufer, M., *Multi-ring sensing electrodes for arrhythmia detection and classification*, in MS Thesis in Biomedical Engineering. 1992, University of Miami: Coral Gables. p. 86.

Kaufer, M., L. Rasquinha, and P. P. Tarjan. *Optimization of multi-ring electrode set*. in *Annual International Conference of the IEEE Engineering in Medicine and Biology Society*. 1990.

Kaufer, M., L. Rasquinha, and P. P. Tarjan. *In vivo detection and classification of cardiac rhythms using concentric ring electrodes*. in *Annual International Conference of the IEEE Engineering in Medicine and Biology Society*. 1991.

Lu, C.-C., *Non-invasive Laplacian ECG detection using active concentric ring sensors*, in Biomedical Engineering. 1998, Miami: Coral Gables. p. 112.

Lu, C.-C. *An Ultra High CMRR AC Instrumentation Amplifier for Laplacian ECG Measurements*. in *Association for the Advancement of Medical Instrumentation*. 1998. Philadelphia: AAMI.

Lu, C.-C. and P. P. Tarjan. *Laplacian electrocardiograms with active electrodes for arrhythmia detection*. in *Annual International Conference of the IEEE Engineering in Medicine and Biology Society*. 1997. Chicago.

Rasquinha, L., *Classification of arrhythmias using specialized concentric ring electrodes*, in MS Thesis in Biomedical Engineering. 1993, University of Miami: Coral Gables. p. 168.

Tarjan, P. P., C. Slocum, and W. Beranek. *Direction independent locally specific permanent electrodes for the identification of arrhythmias*. in *Annual Conv. of the North American Society for Pacing and Electrophysiology*. 1987. Boston.

Tarjan, P P, S M Argnani, C-C Lu and G E Antonioli: *Laplacian Electrograms with Active Concentric Ring Sensors*. In Proceedings: Il Paziente Cardiopatico tra Pratica Clinica e Sviluppo Tecnologico, pp. 51–54. Ferrara, Italy, Jun. 26, 1998.

Argnani, M S, G E Antonioli, C-C Lu, and P P Tarjan: *First Clinical Results with Directly Obtained Laplacian Electrograms*. Heartweb, (Internet publication), January 1999.

Lu, C-C: *Non-Invasive Laplacian ECG Detection Using Active Concentric Ring Sensors*, Ph.D. Dissertation, University of Miami, June 1998.

Besio W., C-C Lu, P P Tarjan: *A Feasibility Study for Body Surface Cardiac Propagation Maps of Humans from Laplacian Moments of Activation*; Electromagnetics, vol. 21, pp. 621–632, 2001.

Besio, W. G.: *A Study Of Laplacian Surface Maps From Moments Of Activation To Detect Cardiovascular Disease*, Ph.D. Dissertation, University of Miami, May, 2002.

Non-analogous methods and systems relating to measurement of heart activity are disclosed in the following non-analogous U.S. patents.

| Pat. No. | Patentee |
| --- | --- |
| 5,146,926 | Cohen |
| 5,797,396 | Geiser et al. |
| 5,938,597 | Stratbucker |
| 6,014,582 | He |
| 6,117,087 | Kamm et al. |

SUMMARY OF THE INVENTION

As will be described in greater detail hereinafter, applicants 3-ring sensors obtain the derivatives directly, without computation. This work led to hand-made isochronal maps of the heart's activity which appeared to provide new insights into the way the depolarization wavefronts propagate through the heart muscle. These were obtained from more than 20 sensor sites, 7 sites recorded simultaneously along with a Lead II EGG. The latter served the purpose of synchronizing the sequentially obtained sets if more than 7 sites were involved. Up to 21 sites have been obtained from a single session. More recently, one of the applicants, W. G. Besio recorded from 35 sites in a regular 5 by 7 array and further improved the density of the data by interpolation. Besio also improved the signal-to-noise ratio (SNR) of the sensors as well as the filtering algorithms and simplified the system. The SNR may be improved further by signal averaging—several consecutive heart cycles with respect to a moving time reference, the peak of the Lead II EGG for each cycle. 30 seconds of digitized data per channel have been used to improve the SNR by a factor of about 5 or 6, depending on the heart rate. The instrumentation comprised the sensors and a laptop computer that was enhanced with an analog to digital (AID) converter and LabVIEW software, to convert the computer into a "virtual instrument" for signal processing, analysis and display. Besio further refined this system by developing new processing algorithms to define the Moment of Activation (MOA) near a sensor. The MOAs are determined with rules developed utilizing fuzzy logic or other means. The MOA corresponds to the instant when the area nearest to the sensor is depolarized. The Moment of Activation was defined as the zero crossing of a Directly Obtained Laplacian Cardiac Electrogram signal. The original method relied on the detection of the baseline crossing of the signal. This was based on theoretical considerations, but in the presence of noise the method needed improvement and more complex algorithms have been developed and tested The curves (or surfaces in three dimensions) connecting simultaneous MOAs are referred to as isochrones. Laplacian potential maps, both for signal averaged heart cycles and sequential single heart beats were also generated by this system. See "FIRST CLINICAL SERIES WITH LAPLACIAN ELECTROGRAMS WITH ACTIVE CONCENTRIC RING SENSORS", by M. S. Argnani et al., "HeartWeb", Vol. 4, No. 3, January, 1999; "An Ultra-High Common-Mode Rejection Ratio (CMRR) AC Instrumentation Amplifier for Laplacian Electrocardiographic Measurement" by Chih-Cheng Lu and Peter P. Tarjan, pp 76–83. January/February 1999 issue of "BIOMEDICAL INSTRUMENTATION & TECHNOLOGY"; and, "Non-InvasiveDetection of Moment of Activation Using Laplacian Cardiac Electrogram Body Surface Mapping System" by G. E. Antonioli et al., pp 382–387, June 1999 issue of "Progress in Biomedical Research", the disclosures of which are incorporated herein by reference.

If one relies on the active sensors' far-field discriminatory behavior, then it is possible to postulate sources near the sensor, which will produce similar signals as the naturally produced data. This appears to be realizable if the instantaneous position of the source at the MOA is along the axis of the sensor. The distance from the sensor to the epicardium, the third part of the coordinate set for the dipole, may be obtained by using ultrasound. This implies that a partially open surface image of the epicardium of the left heart may be obtained non-invasively that depicts both the electrical activity and the instantaneous positions of the sources, as applicants expect to be able to provide the spatial information as well. Such a system provides a novel and economic way for the cardiologist to obtain monitoring and diagnostic data, as well as visual guidance in the delivery of interventional therapies, such as tissue ablation.

Figure 1A:
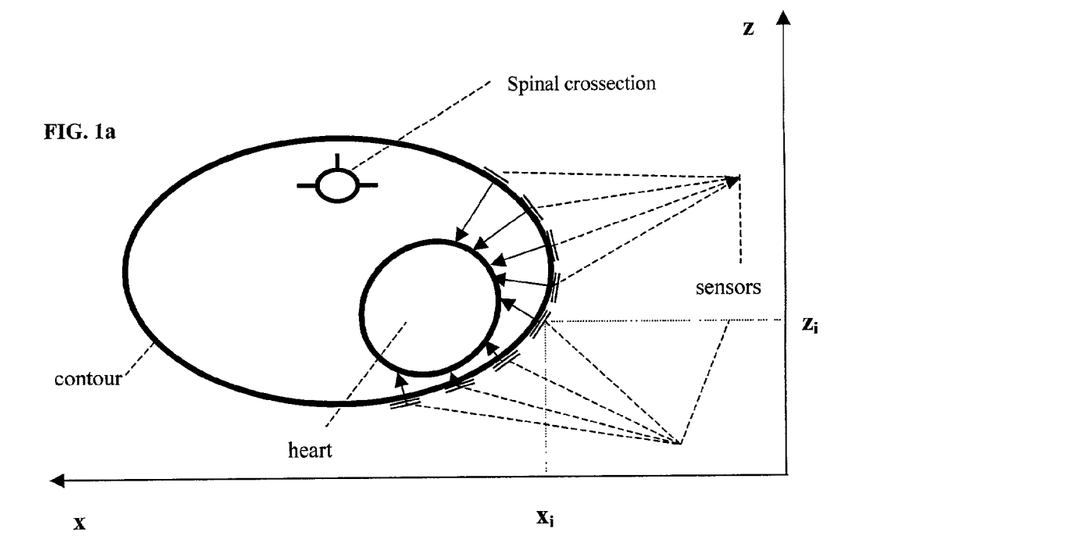
FIGS. 1a, 1b and 1c show the method of detecting the moving surface of the heart with respect to the sensors, and the production of a virtual surface on which the concurrent electrical activity of the heart may be projected to depict kinetic and electrical activity together in a unified manner.
Figure 1B:
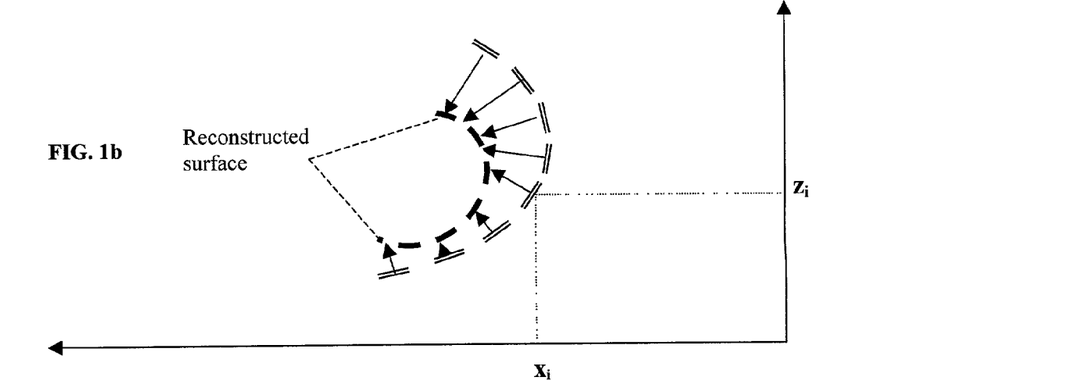
Figure 1C:
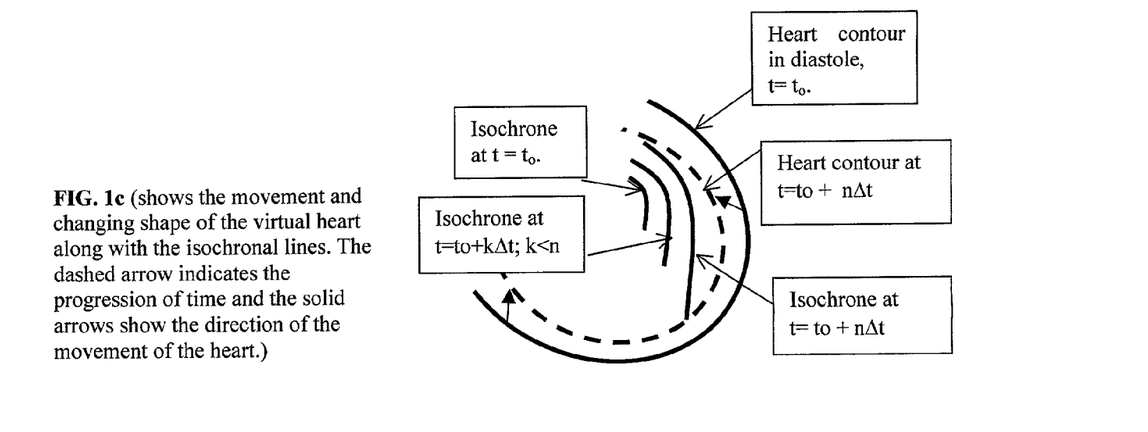

Solutions to the Inverse Problem are clinically useful and important. The "solutions" are enriched if the distances from the center of each sensor to the nearest heart tissue are known. With that information available, one can continuously update the sites of the moving sources. The invention proposes several approaches toward that goal. One preferred approach is to provide for each active Laplacian sensor to be enhanced by an ultrasonic sensor to measure the time a burst of sound travels to and from the moving surface of the heart, as shown schematically in FIG. 1.

The upper panel, FIG. 1a shows schematically the cross section of the torso with the heart. Each of the eight short parallel lines arranged on the contour of the torso represents the combination of an ultrasonic sensor with an LECG sensor, together they detect both the distance of the sensor from the heart's surface and the Laplacian potential at that point. The lower figure shows the reconstruction. The contour also needs to be determined as the sensors are tangential to the contour and the distance to a point on the heart is perpendicular to the tangent at the surface. FIG. 1b, the lower figure, shows the reconstructed and curve matched surface as a dashed line. FIG. 1c illustrates in two dimensions and in a very much simplified manner the display of the moving virtual surface of the heart with the projection of isochronal lines onto that surface. It is self-evident that a two dimensional rendering of a time varying three-dimensional display, or five dimensional display if time and isochronal intensity are included. Such a sketch only provides a very simple illustration of one of the goals of this invention, specifically the simultaneous presentation of spatial and depolarization information about the activity of a heart in health or disease.

Assuming the velocity of ultrasound propagation to be constant in the tissues involved, a fair assumption for the ventral torso (from the front), but compromised by lung tissues for dorsal (from the back) sites, direct measurements of the exact sites of the sensors on the chest surface allow the determination of the position and distance from the center of the sensor to the heart along a line orthogonal to the plane of the sensor. A virtual heart surface is then created and updated at a reasonable rate depending on the available computing speed to show the movement of the heart's surface. At each ultrasonically and LECG monitored site the dipoles may be assigned for the inverse solution to mimic time dependent charges or dipoles at those points, equivalent to moving charges or dipoles on the heart. With that information, 4-D displays of the activity become available the accuracy of the image of the moving heart's surface depends on the number of sensors and the rate at which the spatial data is updated. The result is the appearance of the activation sequence on the virtual surface of the heart. Until quite recently, such concentric electrode configurations have been used for recordings where the active organ, such as the heart, and the electrodes were in direct contact with each other. Such work with three concentric elements connected in a bipolar configuration (the outer and inner elements shorted vs the middle element) to canine hearts was reported by one of the inventors, Peter Tarjan et al. in 1987, followed by the Master's theses of Rasquinha and Kaufer at the University of Miami, in 1992 and 1993. The first recordings of the electrical activity of the heart with three concentric elements on the body surface were reported by Lu et al. in 1997. The three elements were integrated with battery-powered amplifiers and signal processing to reduce interference. These sensors exhibited considerable sensitivity to nearby events and rejected "far-field" activity. The potential difference between the terminals of such concentric electrodes with small gaps between the elements was shown to be proportional to the second spatial derivative of the surface potential, also known as the Laplacian "potential." The dimensions of the Laplacian are in volts/m.sup.2, hence the quotation marks, however, the signal from the sensor is indeed a voltage that is "scaled" by the gaps between the three element. This will be shown in more detail. This method of recording may be referred to as a Laplacian ECG (LEOG). Simultaneous LECG recordings from as many as 7 surface sites were obtained along with a conventional "bipolar Lead II ECG. by Lu in his dissertation and elsewhere (Ph. D. dissertation of C-C Lu. 1998).

The limitation to seven sensors was set by the capacity of the analog to digital converter, A/D and the recording system. The number of simultaneously recorded channels may be expanded to well beyond 50. The ultimate physical limits on the number of sensors and channels are the space available to place sensors on the subject's torso and the size of each sensor as those can not overlap. The diameter of the sensor determines its depth to sense. Besio reported results with up to 35 recording sites on the human torso. (Besio: Ph.D. dissertation; University of Miami, May, 2002.) The present application arises from that work.

In a related area of investigation He et al. reported their results with computing the Laplacian ECG from numerous regularly spaced unipolar sites forming an array for body surface electrograms (BSE). The Laplacian was computed from the differences in simultaneously observed potentials at adjacent electrodes. As the electrode array was typically rectangular, the computed LECGs are expected to be sensitive to the orientation of the axes of the sensors with respect to the travel of the electrical source within the heart.

The "Inverse Problem" in electrocardiography may be stated as a task to define the site, nature and timing of electrical activity within the heart from surface recordings. It is generally considered a problem without a singular solution. However, approximate solutions appear to be valuable for the cardiologist in the analysis of cardiac depolarization patterns, especially in the atria whose contribution to the surface ECG is typically very modest. It is one of the objectives of this application to outline ways to obtain approximate representations of the electrical activity of the heart, displayed in space and time as follows: the LECG at a point on the chest presents the electrical activity from that part of the heart that is closest to the sensor. Other electrically active biological or non-biological sources could be processed in a similar fashion. The LECG provides a signal that is a function of time and unique at the site of observation. That site needs to be identified with respect to anatomic landmarks and the distance between the sensor and the source of the electrical activity represented by the LECG should be known. With that information continuously updated as the heart moves within the chest and the sensors move along with the chest, one may create a map of the electrical activity on the chest surface. The signal's strength is strongly dependent on the distance between the instantaneous position of the "equivalent" moving dipole in the heart and the Laplacian sensor. The signal decreases in proportion to the inverse cube of the distance between source and sensor. The signal amplitude and its spectrum depend on the dimensions of the Laplacian sensor. Sensitivity to activities deeper than the radius of the largest of the sensor's rings is nearly negligible. The spectrum is also more broad when the distance between those is small. The concentric sensors act as low pass filters whose cutoff depends on the source-to-sensor distance.

Combining the signal as a function of time at each sensor's position, using multiple sites, it has been possible to create chest surface maps of isochrones and Laplacian potentials (Ph.D. dissertations of C-C Lu, 1998 and W. G. Besio, 2002). These were obtained both, by signal averaging a sequence of similar heart cycles, and for individual heart beats. Besio's dissertation demonstrated at least two special applications: the activation maps for atrial arrhythmias and for "biventricular" pacemakers.

The isochrones are the curves on the chest surface which indicate the connecting line for simultaneously depolarized zones tissue . Their utility may be in detecting zones of delayed depolarization such as infracted or ischemic areas. The utility of such displays is in diagnosing the site and dimensions of an infarct. The display may also present valuable diagnostic data about the direction of propagation of the activity as those trajectories are orthogonal to the isochronal lines. Using a smaller number of sensors, such as seven sites, the eighth channel for a Lead II ECG allows combining LECGs recorded in sequence from the same sensors but placed in new locations, as long as it is assumed that the beat-to-beat rhythm is relatively stationary, within the range of respiration induced heart rate variability. This assumption is further justified when signal averaging is employed for each sensor to improve the signal-to-noise ratio (SNR). The trigger for the signal averaging process can be derived from a fiduciary point of the standard bipolar surface ECG, such as the peak of the "R-wave" of Lead II. The R-wave is the most pronounced feature of that signal and easy to recognize. Our prior work involved 30 to 60 second long recordings, whose SNR was improved by about a factor of 6 after averaging.

Another objective of the system of the present invention is to monitor the mechanical movement of the heart within the chest in its preferred embodiment or in other embodiments, electrically active biological or non-biological sources, especially with respect to the positions of the LECG sensors. The preferred embodiment is described, but the technology could easily be applied for other applications not described or expressed. The distance between the sensor and the closest part of the heart's surface can be monitored with ultrasonic echo detecting transducers. It is assumed that the speed of sound in the tissues from the body surface to the heart is known well enough to be able to compute the distance traveled from the time the echo from the heart returns to the transducer. This assumption is quite reasonable for the frontal and left lateral portions of the heart, based on the anatomic relationship between the heart and the left lung.

If the distances between a set of LECG sensors to the heart may be monitored in a nearly continuous manner, such as once every 10 ms at each site, then from the instantaneous distances from the position of each LECG sensor, one may create a virtual surface within the chest. The LECG map may then be projected onto this virtual surface, instead of being shown on the chest surface. Correction factors for the magnitude of the signal may be determined from the distance measurements to obtain the final, dynamically changing map of electrical activity on this moving virtual heart surface. Besio's dissertation demonstrated in 2002 the projection of the signals from an array on the body surface to a cylinder that was used as a substitute for the chest. A somewhat modified transformation is used for projecting the LECGs from the surface onto the virtual surface of the beating heart as obtained from ultrasonic measurements.

It is understood that the virtual surface is neither closed nor highly accurate for the two main reasons that the activity of the right free wall of the right ventricle may not be determined accurately either with LECG or ultrasonic sensors; and because the speed of sound in the lungs is different from more dense tissues. These comments also apply to maps of the atria.

Despite these limitations, akinetic zones, such as infarcts or old scarred zones, are expected to be shown stationary while the electrical activity is expected to be delayed and weak from those zones.

Another method of generating a realistic moving surface of the heart employs Doppler phase shift measurements by each single sensor. The phase shift is proportional to the relative velocity of the reflecting surface element on the heart with respect to sensor on the torso. This velocity corresponds to movement along the normal vector from the sensor. The sequence of velocity values can be employed to predict the probable position of the reflecting surface for the next echo determination. The measurement of the distance based on the flight time of the echo provides the actual position of the reflecting element, while the corresponding phase shift provides the information to estimate the next position of the reflective element, and so on.

For the surface maps, the spatial information may be obtained in a relatively simple manner by momentary breath holding to immobilize the sensors. The sensors' locations on the chest may be determined by several different means with respect to anatomic landmarks such as the midline over the breastbone or sternum and by assuming a perpendicular axis connecting the subject's nipples. Other anatomic landmarks may also be used such as certain spaces between specific ribs, etc.

To obtain the virtual heart surface with respect to the sensors on the chest surface, breath holding and similar landmarks may be employed as a frame of reference. The details of this method and variations on it will be described below.

According to the teachings of the present invention, a display of the electrical activity of the heart as a function of space and time for medical use by a cardiologist is developed. Such display will enable the diagnostician to see whether the electromechanical behavior of the heart is normal, and if it is not, then where and when the aberrant behavior originates and how it propagates. The electrical activity of the heart may be viewed at the cellular level as the membranes of the muscle fibers depolarize and repolarize cyclically. The activity may also be viewed as depolarization and repolarization fronts moving through the heart, separating the tissues into polarized and depolarized compartments. As depolarization penetrates the heart muscle volume as a wavefront, the polarized compartment is pushed back, behind the advancing wavefront. However, after a finite period, typically ranging between 200 and 400 ms, the depolarized region returns to the polarized or "resting" state, awaiting the next depolarization wave. Cardiac arrhythmias, such as too rapid, too slow, or irregular rates of depolarization and contraction are associated with diseases of the heart and are studied in the electrophysiology (EP) laboratory by specialists with the aim to understand the aberrant mechanisms and treat those with drugs, devices or by surgical means. The EP studies are usually invasive, that is, electrodes are introduced into the heart or its vasculature to sense local activity. The positions of the sensing electrodes are ascertained by fluoroscopy. These procedures are very time-consuming and carry a variety of risks. The longer the procedure, the greater the risk for complications. Hence, preliminary information about the propagation of depolarization in space and time, even if insufficient for a definitive diagnosis and intervention, appears to be important in saving time, allowing a preliminary diagnosis, and reducing the time spent on the invasive study.

Directly Obtained Laplacian Cardiac Electrograms (DOLCE)

LECG represents the second spatial derivative of the surface potential.

Symbolically $\nabla^2 \Phi$ stands for this second spatial derivative of the potential.

In Cartesian coordinates:

$$\nabla^2 \Phi = \frac{\partial^2 \Phi}{\partial x^2} + \frac{\partial^2 \Phi}{\partial y^2} + \frac{\partial^2 \Phi}{\partial z^2}$$

where $\Phi$ is the potential and it is a function of time and space, $\Phi(x,y,z,t)$.

According to Poisson's equation [Guirajani: *Bioelectricity and Biomagnetism*, p. 197, 1998], assuming that electrical current sources exist in a volume:

$$\nabla^2 \Phi = \frac{\nabla \cdot J}{\sigma}$$

where $\nabla \cdot J$ represents the divergence of the current density, namely the sources that generate the current in the chest that gives rise to $\Phi$, the potential in the chest, a volume conductor, whose conductivity is $\sigma$. In this formulation the conductivity is assumed to be homogeneous. As the current density arises from sources within the heart, in the region outside the heart that includes the surface of the chest where $$\nabla_s^2 \Phi = 0$$

The boundary of the body (unless it is immersed in a conductive fluid, such as seawater) prevents current flow across the surface, hence $J_n$ the normal component of the current density at the surface is zero.

For this reason $$\nabla^2 \Phi = \frac{\partial^2 \Phi}{\partial n^2} + \frac{\partial^2 \Phi}{\partial \xi^2} + \frac{\partial^2 \Phi}{\partial \eta^2} = 0$$

at the surface.

The negative of the surface Laplacian in the tangential plane represents the discontinuity in normal current at the surface point $(\xi,\eta)$. The value of this is made up of two orthogonal components and could be computed from the potentials at adjacent point electrodes in an array on the body surface. Instead of computing the value of the Laplacian from small differences, we have adopted a method to obtain directly the local Laplacian by placing either two, or three concentric elements at the site as shown in FIG. 2a and FIG. 2b and connected as shown.

The Laplacian map is a two-dimensional plot of the local value of the surface Laplacian at each spatial ($\xi$ and $\eta$) coordinate that varies with time. The time dependence arises from the heart's depolarization and repolarization, where n is a vector normal to the body surface and pointing into the body. At that point the Laplacian corresponds to the second spatial partial derivative with respect to the radial displacement in the plane tangential to the body surface at (ξ; η).

DETAILED DESCRIPTION OF THE INVENTION

Figure 2A:
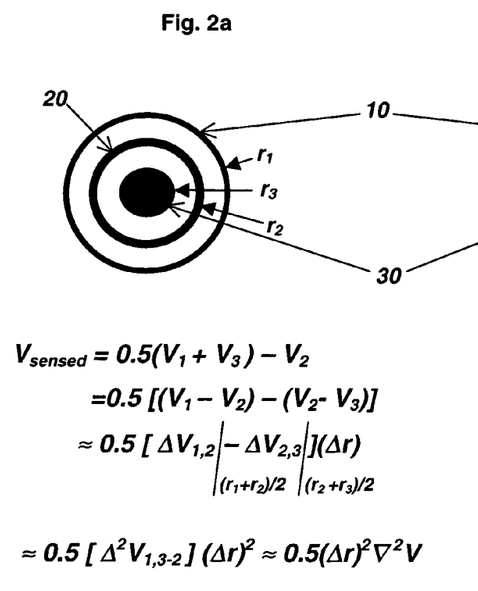
FIGS. 2a and 2b show two concentric electrodes which are used to sense surface potential on a body and shows equations related to the second partial derivatives of the surface potentials.
Figure 2B:
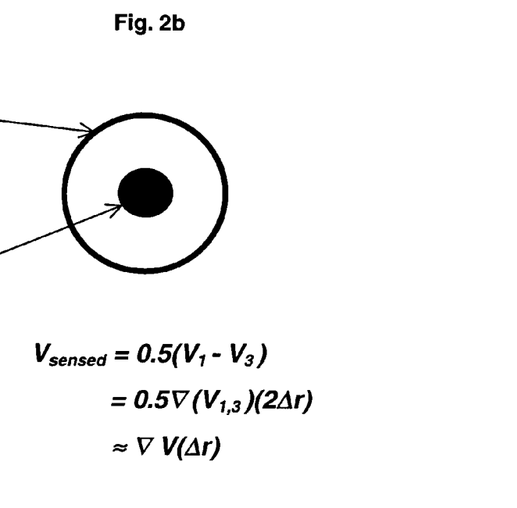

Referring to the drawings in greater detail, FIG. 2a, represents the core idea in Laplacian recordings. The idea is that the "Laplacian" detects the second spatial partial derivative of the surface potential on the body. It is defined in Cartesian coordinates as:

$$\frac{\partial^2 V(x,y)}{\partial x^2} + \frac{\partial^2 V(x,y)}{\partial y^2} + \frac{\partial^2 V(r)}{\partial r^2}$$

where V(x,y) is the surface potential at x,y versus some reference potential, such as the right ankle.

The computational method adopted by Bin He at the University of Chicago approximates this Laplacian by measuring potentials (ECG values) at specific points (x,y) on a matrix and computing the differences at a given time.

Δx=Δy

These small electrodes of about 2 to 5 mm diameter are placed on the chest surface. The distance, Δx, between adjacent electrodes is about 10 mm in He's setup.

The computed approximate Laplacian obtained is as follows:

The computed Laplacian ECG is proportional to:

$$\left[\left[\frac{V(x_{i+1}, y_i) - V(x_i, y_i)}{\Delta x} - \frac{V(x_i, y_i) - V(x_{i-1}, y_i)}{\Delta x}\right]^2 + \left[\frac{V(x_i, y_{i+1}) - V(x_i, y_i)}{\Delta y} - \frac{V(x_i, y_i) - V(x_i, y_{i-1})}{\Delta y}\right]^2\right]$$

The value of the Laplacian is somewhat dependent on whether the computation is based on the differences along the x and y directions or along the diagonals of the array. They are not the same! Also, as it computes the difference between almost the same values, small errors in the digitized values at each point can produce large errors according to "the tyranny of small differences"—a derogatory term for computing—rather than measuring small differences. (It is the problem of determining whether one of two identical twins is bigger than the other. If you place them on a scale one by one against weights, the error may be larger than the difference between the babies. It is best to put the babies on a balance simultaneously to determine which way the scale tips.)

In contrast, applicants use three concentric electrodes. The inner and the outer electrodes are shorted with the assumption that on a conductive electrode the potential is uniform, hence the two shorted rings would be at a given instant at the potential that represents the average potential for the areas those electrodes contact, $[V_a=(V_{outer}+V_{inner})/2]$. The average of the inner-outer pair of elements, minus the intermediate ring $V_i$, represents the Laplacian potential. This is a very small amplitude signal as $V_a$ and $V_i$ are almost the same except when the source of the potential is in the vicinity of the sensors. FIG. 2a shows the concentric electrodes used.

As the Laplacian signal is proportional to the square of the gap, the Laplacian signal is small in amplitude even from sources in the vicinity of the sensor. On the other hand the Laplacian sensor is insensitive to interference from a source remote from the sensor. Amplification of the signal is necessary before further processing. Mr. Chih-Cheng Lu developed a self-contained amplifier and band-pass filter that was reduced to such a small size that the electronic circuits and a 2-cell lithium battery all fit on the back of the sensor. Through a miniature cable, the sensor could be interfaced with an A/D converter and the "directly," in contrast with "computationally," obtained LECG (or Directly Obtained Laplacian Electrogram: DOLCE) data was stored in a computer memory at the sampling rate of 1000 samples/channel/second.

$$\frac{V(x_{i+1}, y_i) - V(x_i, y_i)}{\Delta x} - \frac{V(x_i, y_i) - V(x_{i-1}, y_i)}{\Delta x} \propto \frac{\partial V(x,y)}{\partial x}\bigg|_{x=x_i+\Delta x/2} - \frac{\partial V(x,y)}{\partial x}\bigg|_{x=x_i-\Delta x/2}$$

$$\propto \frac{\partial^2 V(x,y)}{\partial x^2}\bigg|_{x=x_i}$$

Similarly:

$$\frac{V(x_i, y_{i+1}) - V(x_i, y_i)}{\Delta y} - \frac{V(x_i, y_i) - V(x_i, y_{i-1})}{\Delta y} \propto \frac{\partial V(x,y)}{\partial y}\bigg|_{y=x_i+\Delta y/2} - \frac{\partial V(x,y)}{\partial y}\bigg|_{x=y_i-\Delta y/2}$$

$$\propto \frac{\partial^2 V(x,y)}{\partial y^2}\bigg|_{y=y_i}$$

Lu's design provided a gain of 1000 and SNR of nearly 120 dB. Besio further improved the design by reducing the noise level, and improving the SNR.

Lu's design was suited for signal averaging, using the QRS of the Lead 2 ECG. The typical recording was 30 seconds long with about 30 to 50 heartbeats. As the SNR improves with the square root of the number of events, the SNR improved by a factor of 5 to 7 when Lu's records were signal averaged.

Besio's sensors are more quiet and offer more gain, hence it was possible to record and process the signals for a single beat, without signal averaging. This feature enabled Besio to obtain signals from atrial depolarizations without signal averaging.

Monica Kaufer's MS thesis dealt with the optimization of the geometry of the sensor. Her work showed that the optimal size for the radius of a sensor's outer electrode is d for detecting depolarizations d distance below the surface.

Based on her work, the "active" electrodes, those with their integral amplifiers and filters, were designed to be 36 mm diameter by both Lu and Besio.

Lu experimented with a 2-element sensor, as shown in FIG. 2b. That configuration yields a larger output that is proportional to the gradient of the potential, or the approximate electric field intensity at the center of the sensor.

An analysis of the geometry of coordinate systems moving with respect to one another is set forth below.

If $S_j(x_j, y_j)$ designates the center of the $j^{th}$ sensor on the torso, then $z_j$ is the distance from the center of the DOLCE sensor to the heart. That point on the heart may be designated as $P_i(x_i, y_i, z_i)$ where $z_i$ is the "depth" of the echo-generating site within the torso. The metric $d_j(t)$ is the instantaneous distance between $S_j$ and $P_i$. With reference to the $P_i$ points serving as the apices of a polyhedral surface, virtual surfaces of the epicardium and the endocardium may be constructed in real time, with frequent updates of the surface. This process may include the estimated sites of the points of reflection of the echo on the surface of the heart on the basis of Doppler phase shift measurements as explained earlier. The virtual surface derived from these ultrasonic measurements will result in a distorted image as the surface of the torso is stretched into a plane to form a map. However, there are other ways, using ultrasound, to determine the positions of the echo generating tissue zones. These will also be described. The frequency of updates will be limited by such factors as the transit time for ultrasound and computational speed. The distances from the torso's surface to the heart are on the order of 10 to 100 mm, hence at the typical speed of sound in soft tissues, 1.54 mm/microsecond, the transit times are on the order of a fraction of a millisecond.

It may be noted that the resolving power of ultrasound is proportional to the frequency of the ultrasonic oscillations while the depth of penetration diminishes with increasing frequency. For example, the wavelength of an 8 MHz wave is close to 0.2 mm but its penetration is limited to approximately 20 mm. If the transducer is used for probing at 40 mm, the signal becomes severely attenuated. A more traditional frequency, such as 1.5 MHz would offer lower resolution around 1 mm, but it would be suitable to probe the heart even from dorsal sites.

Using software already developed, 3-D, 4-D or 5-D presentations may be constructed with respect to the needs and expectations of a clinician. 4-D provides isochronal contours evolving on the virtual image of the beating heart. Five dimensions include the three spatial coordinates for each site on the heart contributing to the virtual image, along with the Laplacian potential evolving as a motion picture as a function of time. This may be visualized as if there were two separate but interlocked sensing systems operating. One of these consists of a set of sensors on the body surface collecting and processing Laplacian signals from a finite set of points confined to the body surface. The other system monitors the movements of the heart's surface and the positions of the Laplacian sensors. The data is converted into a virtual surface that moves in a coordinate system of choice, such as the frame of the laboratory or an anatomic landmark in motion, such as the xiphoid process in the chest. The LECG activity may then be projected onto the virtual image of the surface of the heart. The challenge of presenting these values is first met by constructing a 3-D virtual model of the heart for projection on a screen and use of colors to indicate the magnitudes of Laplacian potentials as they evolve and move over the heart until they are extinguished.

It should be noted that in the normally beating heart depolarization precedes muscle contraction, hence during the depolarization phase, while the LECG is most pronounced, the normally beating heart is at the end of its filling phase and relatively stationary. In a slowly beating heart the "screen" for projection is stationary. However, the moving surface during the entire heart cycle would enable the physician to visualize the relationship between akinetic and active zones. At fast heart rates, tachycardias, the electrically active and mechanically active phases of the heart cycle tend to overlap more. This dual detection system would prove very useful in the study and diagnosis of such pathological cases.

The method of combining the ultrasonic and Laplacian sensors offers certain advantages. The reference point for the LECG is locked to the origin of the distance measurement to the epicardial surface. However, there are other ways to obtain spatial changes.

Figure 3:
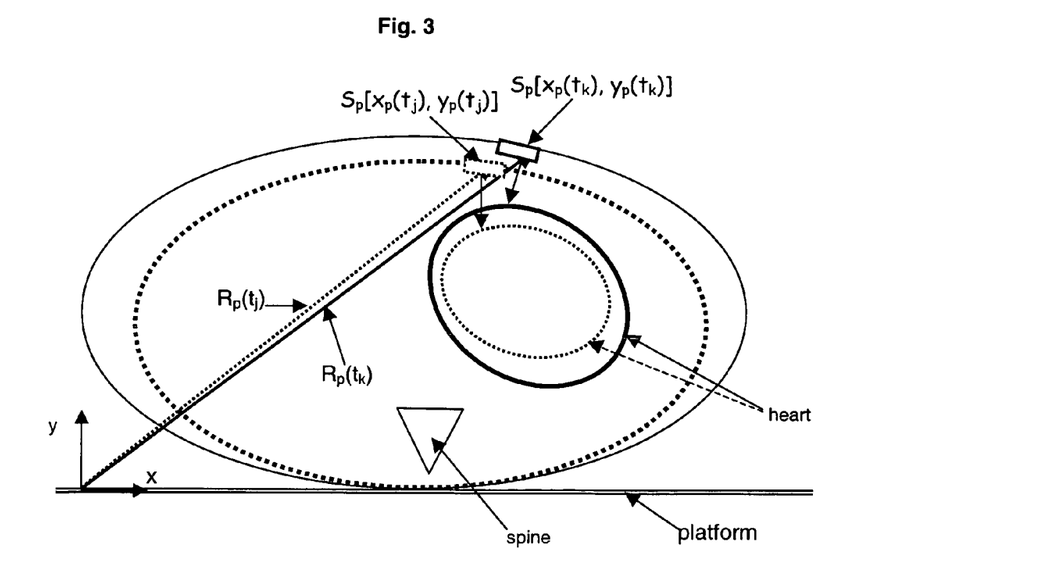
FIG. 3 is a depiction of the movement of two fuzzily defined points on the surface of a heart.

The detection of the motion of the heart is not trivial as the B-mode detectors provide displacements between two sets of fuzzily defined points as shown in FIG. 3.

The vector of concern, normal to both, the surface of the sensor and the body surface (if properly applied), points from the center of a sensor along the ultrasonic beam toward the surface of the heart, where it terminates at the intercept of the beam with the heart.

As both, the torso's surface and the heart's surface change with time, the surface of the heart should be described in a framework that is either referenced to the subject's stationary anatomy, such as the spinal column, the xiphoid process, or alternately, to the table. The sketch shown in FIG. 3 is exaggerated. The solid curve of the two larger ellipses represents one of the changing cross sections during the respiratory cycle of the chest, while the smaller solid ellipse represents the cross section of the heart at the same instant, $t=t_j$. The dashed ellipses correspond to those same anatomic surfaces at a different time, $t=t_k$. The small rectangles represent the two positions of a single sensor ($S_p$), which is assumed to be affixed to the chest surface and can move not only within the cross section, but even in a direction perpendicular to the cross section.

The beam is assumed to be orthogonal to the sensor, the distance measured between the sensor's center and its beam's intercept with the epicardium, at each instant, is different. The measurement of the distance that corresponds to the length of the vector r.sub.p(t.sub.j) yields the distance from a moving point on the chest to the moving surface of the heart, but the vector is "not stuck" on a specific moving point on the heart, it does not point to the exact same tissue element. However, that does not matter because it is the electrical activity at the point where r.sub.p points at t=t.sub.j that is of interest in the overall imaging of the electrical and mechanical aspects of heart activity. In other words, to create an exact dynamic reconstruction of the heart's surface in a stationary coordinate system, we must also know where the sensor's center is in our chosen framework (where R.sub.p(t.sub.j) points), as well as the relationship of the sensor to its neighboring sensors. The tissue element of concern is where the vector sum of R.sub.p(t.sub.j) and r.sub.p(t.sub.j) points. That point may be defined by the vector in the x,y coordinate system of the table (not shown). H.sub.p(t.sub.j)=R.sub.p(t.sub.j)+r.sub.p(t.sub.j) for t=t.sub.j, where $H_p(t_j)$ points to the intercept of the beam from the $p^{th}$ sensor with the heart's surface. The vector pointing from sensor p to sensor q may be described as $$S_{p,q} = S_p - S_q$$

which yields the inter-sensor distances on the body surface, time varying quantities.

This is a classical multi-body problem that is very difficult to track precisely unless certain assumptions are made. One might assume that the motion of the thorax is negligible during quiet breathing, only the heart is in motion and being deformed continuously within the torso.

If this were too restrictive then one might assume that the initial positions of the sensors on the torso are well defined within the coordinate system of the table and their positions change in a mutually dependent manner. For instance, if the distance between a pair of sensors were monitored, then the relative displacements in the positions of all the others, with respect to the initial set, will be computed as if the surface of the chest were to expand or contract as an isotropic shell. (Three points forming a triangle on the surface of the torso with sides a1, a2 and a3 will all increase proportionally. The array of the sensors may be described as an expanding and contracting 3-D surface constructed with a wire mesh of triangles.). This still allows displacement of the entire network of sensors with respect to the table!

One may also choose to monitor two or more sensor locations with respect to the table as a reference and adjust the positions of the other sensors accordingly.

The final task is to determine the movement and deformation of the heart's surface from the ultrasonically measured scalar values, $|r_p(t_j)|$, as a function of time, but with respect to the table's coordinate system and in reference to the instantaneous position of the corresponding sensor, $R_p(t_j)$, in the array of sensors on the chest. In other words, the following data needs to be available for each increment of time:

$$R_p(t_j) = x_p(t_j)u_x + y_p(t_j)u_y + Z_p(t_j)u_z \text{ (u is a unit vector)}$$

the orientation of the normal vector $n_p$ to the sensor's, $S_p$'s plane at $R_p(t_j)$, the position of the intercept of the beam from $S_p$ with the heart in the table's coordinate system:

$$R_p(t_j) + |r_p(t_j)|n_p$$

the value of the electrical activity as detected at $S_p$.

From these pieces of data, the surface of the heart and the corresponding potential distribution on it may be displayed.

The distance from the sensor to the heart's surface—not necessarily a specific point in the heart's anatomy, but the shortest distance at the instant of the measurement from the sensor to the heart, is yielded by the ultrasonic B-mode distance measurements. This may be further complicated by the changing orientation of the sensor with respect to the tangent of the torso's surface at the point of attachment of the sensor.

Some of these problems may be dismissed or simplified by placing the sensors on the inside of a relatively stiff garment, a vest, sufficiently inelastic to limit the movement and retain the sensors' orientation with respect to the torso's surface.

Another approach may be based on a variation of the "Biosense" technique used by the invasive electrophysiology system (originated in Israel, and presently owned by Johnson & Johnson-Cordis-Webster), where the coordinates of $S_p$ may be obtained with an electromagnetic locator. (A set of mutually orthogonal RF fields is created at different frequencies. The induced voltages in the 3 added sensing coils of each sensor must be processed to determine the sensor's instantaneous location and orientation.)

Another simplification of the localization of the sensors may come from using a marker on the chest and obtaining digitized images of one or two projected moiré patterns of the chest to determine the "resting positions" of the sensors automatically.

As a practical starting point one may simply measure the circumference of the torso with a cloth measuring tape and the distance from the table to the sternum. With those piece of information one may simply assume that the cross section is elliptical and place the sensors along intercostal lines to prevent the ribs from obstructing the ultrasonic beam's path.

While these are challenging problems, the concept of creating an approximate 3-D image of the heart defined by a polyhedron on which the electrical activity may be displayed, is viable and is useful for the practicing clinician. It is non-invasive and provides information that can only be obtained invasively at this time. Even a relatively simple and technically feasible system, such as the display of the electrical and mechanical activities in sequence, as follows, would provide a novel way for the physician to gain insight into the activity of the heart in a non-invasive manner:

a. Using ultrasonic techniques, obtain a 3-D surface of the heart at the end of diastole;

b. Project the electrical activity from the LECG process onto this surface as a set of isochrones. (This may be shown with contours with color-coding the time with respect to the peak of the R-wave, or as a single generic isochronal line as it moves through the surface.

c. Once the isochrone disappears, the display switches to a 3-D display of the heart's surface as it changes during systole and early diastole.

For comparison, one may consider the limitations of the invasive techniques in use today. The Biosense system marketed by a Johnson&Johnson subsidiary, comprises a combined electromagnetic position and electrical activity sensor at the tip of a catheter that is guided into one of the heart's cavities, the right atrium, for instance. While the tip is maneuvered and the sensed electrical activity through its tip is monitored, the physician decides when the position of the sensor should be read out. At that instant the position is read out of the sensor (with respect to the table used for the procedure as the field's generators are attached to the table) and stored as a point on the endocardium along with the electrogram, using a feature of the surface ECG as a time reference, such as the peak of the R wave in Lead II.

This process is then repeated many times ranging from 25 points to as many as several hundreds of points. While the tip's position is known accurately within the framework of the table, the heart and the torso are in constant motion. Therefore the polyhedron created from those points in the heart is likely to be a distorted image of the actual cavity. This error is acceptable as long as the physician is able to guide the tip back to any desired point with moderate effort.

It is thus evident that the non-invasive system disclosed is not to be compared with an idealized, accurate invasive system that is enhanced by X-ray images as well, as such systems do not exist. Invasive systems carry their own inaccuracies due to moving coordinate systems. (The electrodes move with the heart, but the heart moves within the chest and the chest moves with respect to the reference framework, the room or the table.)

One added complication for the non-invasive system is that the ultrasonic sensors need to face only soft tissues toward the heart, i.e., the sensors must be placed over the gaps between adjacent ribs, or in places where the rib cage does not interfere with the view of each ultrasonic beam. Such places exist in the armpit and sub-costally, pointing toward the head.

A 3-D phased array in the auxiliary region is one solution, where a relatively full and for the purpose, entirely adequate view of the heart may be obtained within the thoracic cage. That array may also be used for determining the changing positions and orientations of the sensors mounted on the chest surface.

To summarize: with a supine subject, resting and quietly breathing, the torso with the sensors mounted on it may be considered stationary and the contour of the chest's cross section elliptical with the perimeter and minor axis defining those as well as the normal vectors to the chest. The scalar measures of the sensor-heart distances may then be used as obtained, uncorrected, to create the contour surface of the epicardium, a virtual beating heart, on which the MOA maps are displayed.

RANGE OF APPLICATIONS

The system and method of the present invention finds utility in guiding the operator, a physician, in the placement of an invasive catheter's active electrode(s) to the site of action, for instance, for cardiac tissue ablation.

The system is expected to find applications in pediatric cardiology and neonatology for which the directly observed Laplacian technique seems especially appropriate.

The effects of certain antiarrhythmic drugs may be monitored with a pair or more of sensors to measure delays in MOA's as a manifestation of the drug's effect.

Besio's dissertation showed that the sensors do respond to atrial activity and may be used to depict atrial activity. This may enable simplifications in the non-invasive diagnosis of atrial arrhythmias, especially in combination with monitoring the atrial wall motion as a way of strengthening the validity of the detection of atrial depolarizations.

Initially applicants explored tripolar concentric sensors for use in the detection of ventricular arrhythmias and fibrillation using sensors sewed to the epicardium and making the decisions for electrical interventions on the basis of triangulation. This method may be used with surface electrodes for the determination whether to defibrillate or not. This may meet the requirements for an Automatic External Defibrillator, such as the ones used at airports and sport stadiums. Triangulation may be used with surface electrodes for the determination whether to defibrillate or not. It may also be used to quantitate the level of ischemia preceding or following an infarct and monitoring the progress with clot resolving agents. This tool is likely to be proven more reliable when combined with the monitoring of wall motion. The absence of ventricular wall motion confirms the diagnosis of VF from electrical signals.

Noninvasive detection of atrial activity will simplify the analysis of ECG data from ambulatory monitoring that relies entirely on ventricular signals.

Ultrasonic Techniques for a 3-D Image

There are several ways of using the positions of the active sensors on the chest surface. In each case the distances from the center to the nearest moving surfaces of the heart, the epicardial surface (or the pericardial sac) and the endocardial surface are measured with ultrasound:

One may assume that the body is stationary during the recording and respiration only plays a secondary role in altering the sites of the sensors. In this case, using some anatomic landmarks (for instance, the midsternal line as one axis and the line connecting the subject's nipples as a perpendicular axis) one can measure the sites of the sensors with a flexible ruler within roughly ±5 mm accuracy. The topographic information may be used as a flat map, with the understanding that there will be distortions due to lack of axial symmetry and variations in the cross-section of the thorax in the region of interest, with respect to the long axis of the body. This method was used for applicants "hand-crafted" activation maps.

One may affix the sensors to the inside surface of a relatively stiff, vest, "binder" or corset. In effect, that will force the subject to use only the diaphragm for respiration. This will force the thorax to follow a form forced on it and may be unacceptable for many subjects, especially those with respiratory difficulties. The predetermined positions of the sensors on the stiff binder will provide the sites on the surface with respect to some anatomic landmarks, such as the midsternal line and another one along the long axis, such as an anatomic landmark used for tracheostomy, the highest point on the sternum, or some clavicular landmark.

One or more scanning ultrasonic "master" sensors may be utilized to determine the site of each active LECG sensor on the unconstrained three-dimensional surface of the chest. That information, $S_p(x,y,z,t)$ for the $p^{th}$ sensor, along with the orientation of that sensor and the distances $d_{p,epi}(t)$ ($=|r_p(t)|$) and $d_{i,endo}(t)$ (referring to the echo from the inside wall) will yield spatial data to generate two open polyhedra that approximate the epicardial and endocardial surfaces of the heart as it beats. This approach will permit the display of the changing wall thickness of the beating heart, with the electrical activity spreading on the outer surface.

Each active sensor may include an ultrasonic gauge that receives echoes not only from the soft tissue interfaces but also from 2 or preferably 3 landmarks attached to the thorax. Thus each sensor will provide its own position within a stationary frame of reference and the positions of the nearest epicardial and endocardial points on the heart. Again, a time dependent, pulsating, open polyhedron may be formed as a surrogate surface for each, the endocardium and epicardium of the heart, with the LECG (DOLCE) data shown either as Laplacian potentials, isopotentials or compressed into a temporally averaged surface with the isochrones displayed on that.

The electromagnetic or magnetic field based position detection system in use in fighter aircraft and in medical applications may be adapted, as described earlier, to locate each sensor and its tilt within the frame of the room, rather than some anatomic landmark.

Another possible method for gaining information about sensor locations could be comprised of an array of elastomer straps whose resistance varies proportionally to the amount they are stretched. As the persons body distorts from breathing or other movements, this information would be captured by this array and used to update information about where the sensors are at a particular moment.

The accuracy of the image of the surface of the heart may further be enhanced by incorporating Doppler sensors for each, or even for some of the ultrasonic sensors. The Doppler technique, based on a shift in the frequency of the returning pulse from the emitted one provides the velocity of the reflecting element along the line of the beam. If the element is moving toward the sensor, the frequency shift is positive. These shifts are proportional to the velocity, hence the system could be enhanced by a predictive feature by extrapolating from the instantaneous position and velocity data where the next position would be expected. Such techniques are well established in Doppler flow systems.

Displaying the Information

The 4-D or 5-D presentations must be constructed in the best possible way to fit the needs of a clinician. These five dimensions include the three coordinates for each apex on the polyhedron along with the potential as a function of time. Presentation of these values requires a 3-D model projected on a monitor's screen, or preferably a holographic display, using gray scales or colors to indicate potentials and using an animated model of the heart, in essence: a motion picture, to show the spread of depolarization with time directly on the virtual surface of the heart.

In summary, the 3-D image of the moving surfaces of the heart may be implemented at various levels of technical sophistication, resulting in different levels of accuracy and cost. The common feature of these approaches may be summarized as follows:

The electrical activity of the heart may be tracked simultaneously on a virtual surface that represents the beating heart within the intact chest. This type of presentation of the electromechanical activity of the heart has not been available to cardiologists either non-invasively, or in real time.

The currently available Biosense system and its competitors gather spatial and electrical data invasively, using a temporary lead within the heart.

The polyhedral representation evolves stepwise and slowly, although the number of points is virtually unlimited.

The risk of complications tends to increase in proportion to the length of an invasive process.

Also, the polyhedron produced is static, it does not change with the deformations and movements of the beating heart.

The technical problems of generating the virtual surfaces of the heart and the display of the electrical activity have been worked out in rudimentary form.

Fast computing techniques will have to be employed to achieve cinematic quality with high resolution. However, the novel concept represents the foundation arising from the merging of electrical and ultrasonic signal processing technologies.

OTHER APPLICATIONS

In addition to noninvasive diagnostic applications, applicants foresee invasive applications as well.

In the noninvasive category detection of atrial activity during atrial flutter and fibrillation are useful.

The organization of contractions may be studied in relation to the sequence of depolarizations. This appears to be suited for the estimation of the size of an infarct.

With an interventional catheter placed in the heart or in a coronary vessel, such as a balloon angioplasty catheter, non-invasive monitoring of the regional activity in the zone subjected to treatment may serve an important role to compare electromechanical activity before and after angioplasty. Fluoroscopy does provide a projection of the moving heart but information about the level of electrical viability is missing.

One may envision electrical ablation to be performed without the need for multiple leads in the heart which are used for spatial and temporal references.

Three or four broad technical issues can be addressed:
1. The optimal way to obtain information about the instantaneous shape and position of the heart?
2. Where to place the sensors?
3. The cardiac conditions and applications of the greatest interest to cardiologists and how to provide that information in a friendly and informative graphic display?
4. Finally, the optimal level of automatic or "expert" interpretation that will allow rapid acceptance of the instrumentation with minimal retraining of the physicians, nurses and emergency care providers.

From the foregoing description, It will be understood that the method system and apparatus of the present invention have a number of advantages, some of which have been described herein and others of which are inherent in the invention.

For example, the method and system enable one to determine in a non-invasive manner, the general location of a site of cardiac activity one is looking for in the heart for any desired purpose, such as locating a point in the heart for ablating tissue.

Also it will be understood that modifications can be made to the method, system and apparatus of the present invention without departing from the teachings of the invention. Accordingly the scope of the invention is only to be limited as necessitated by the accompanying claims.

The invention claimed is:

1. A method of presenting concurrent information about the electrical and mechanical activity of the heart using non-invasively obtained electrical and mechanical cardiac activity data from the chest or thorax of a patient comprising the steps of:
placing at least three active concentric ring Laplacian ECG sensors at locations on the chest or thorax of the patient, each sensor having at least one outer ring element and an inner solid circle element;
placing at least one ultrasonic sensor on the thorax where there is no underlying bone structure, only tissue, and utilizing available ultrasound technology to produce two or three-dimensional displays of the moving surface of the heart and making direct measurements of the exact sites of the sensors on the chest surface to determine the position and distance from the center of each sensor to the heart along a line orthogonal to the plane of the sensor and create a virtual heart surface;
updating the measurements at a rate to show the movement of the heart's surface;
monitoring at each ultrasonic sensor site and each Laplacian ECG sensor site the position and movement of the heart and the passage of depolarization wave-fronts in the vicinity;
treating those depolarization wave-fronts as moving dipoles at those sites to create images of their movement on the image of the beating heart's surface; and,
displaying the heart's electrical activity on the dynamically changing image of the heart's surface with the goal to display an approximation of the activation sequence on the beating virtual surface of the heart.

2. The method of claim 1 comprising the further steps of creating chest surface maps of isochrones and projecting those isochrones onto a virtual surface that represents the heart, which can indicate simultaneously depolarized zones for detecting zones of abnormal depolarization and contraction patterns.

3. The method of claim 1 comprising the further steps of creating Laplacian isopotential maps on the chest surface or by projecting the map onto a virtual and moving heart surface.

4. A method of measuring, analyzing and visualizing electrical and mechanical activities in a system comprising the steps of:
   a. collecting signals over a part of a surface of the system using a plurality of active concentric ring Laplacian sensors, where each sensor has at least one outer ring element and an inner solid circle element and a data acquisition unit,
   b. collecting ultrasonic information about the distance from each sensor to the surface of the moving heart below the each sensor
   c. determining the positions of the sensors,
   d. reducing measurement noise in the collected signals with digital filtering algorithms,
   e. computing and monitoring the equivalent moving dipoles which generate the detected signal at the Laplacian sensors and their positions from the ultrasonic image of the heart; and,
   f. displaying simultaneously still images of the processed signals in both the time and space domains, together with the virtual image of the object of signal origination forming a moving image, and,
   g. updating the measurements periodically to show the movement of the object of signal origination.

5. The method of claim 4 wherein said steps (a) to (g) are repeated for sequential time epochs.

6. The method of claim 4 wherein the system is a biological system.

7. The method of claim 4 wherein the charges or dipoles originate in the heart of a creature.

8. The method of claim 4 wherein the charges or dipoles originate from some other organ in the body of the creature that can be sonated.

9. The method of claim 4 wherein the signals recorded from the Laplacian ECG and the ultrasound sensors are digitized and stored.

10. An apparatus for measuring, analyzing and visualizing electrical and mechanical activities in a biological system, comprising a plurality of sensors and ultrasound transducers for detecting signals over part of a surface of a biological system, such as an internal organ,
    means for collecting the detected signals,
    means for determining positions of the sensors,
    means for determining the Moments of Activation (MOA's) of the collected signals,
    means for determining the surface of interest in the ultrasound image,
    means for reducing measurement noise by applying digital filtering algorithms, and
    means for displaying the spread of electrical activity on the image of the surface of the moving heart dynamically.

11. The apparatus of claim 10 further including means for analyzing the electrical and mechanical activities for sequential time epochs.

12. The apparatus of claim 10 further including means for analyzing the electrical and mechanical activities sequentially, using a stationary image of the heart during the display of the electrical activity, followed by the display of the contracting and relaxing surface of the object of signal origination.

13. The apparatus of claim 10 wherein the means for collecting the signals and the means for determining the MOAs and the means for determining the surface of interest include, respectively, a plurality of concentric ring Laplacian ECG sensors where each sensor has at least one outer ring element and an inner solid circle element and the ultrasound transducers.

14. The apparatus of claim 10 wherein the plurality of sensors further includes an array of magnetic sensors.

15. The apparatus of claim 10 wherein the plurality of sensors includes an array of magnetic sensors and an array of concentric ring Laplacian ECG sensors.

16. A method for processing ultrasonic data from at least two ultrasonic transducers and electrical signals from multiple concentric ring Laplacian sensors each having at least one outer ring element and a center circle element and arranged near a heart to sense movements of a heart including the steps of: combining the ultrasonic data to detect the distance between the a sensor and its target, as well as the a Doppler shift to be used for predicting the corresponding a position of a reflecting surface for a consecutive pulse of ultrasonic data resulting in the actual position of the the portion of the surface of the heart that generates the electrical signal; and further combining an image of the heart's surface with a Laplacian potential isochronal maps.

* * * * *